United States Patent [19]

Fabricant et al.

[11] Patent Number: 4,632,103
[45] Date of Patent: Dec. 30, 1986

[54] BANDAGE TO REDUCE BUNION PAIN THEREWITH

[75] Inventors: B. Robert Fabricant, North Hills; Eli Elias, Great Neck, both of N.Y.

[73] Assignee: Barbara Ann Fabricant, North Hills, N.Y.

[21] Appl. No.: 797,985

[22] Filed: Nov. 14, 1985

[51] Int. Cl.⁴ .............................................. A61L 15/00
[52] U.S. Cl. ..................................................... 128/157
[58] Field of Search .......................... 128/157, 155–156

[56] References Cited

U.S. PATENT DOCUMENTS

| | | | |
|---|---|---|---|
| 772,197 | 10/1904 | Weaver | 128/157 |
| 804,406 | 11/1905 | Hungad | 128/157 |
| 911,823 | 2/1909 | Krieger | 128/157 |
| 1,175,718 | 3/1916 | Crowe | 128/157 |

*Primary Examiner*—Gregory E. McNeill
*Attorney, Agent, or Firm*—Erwin S. Teltscher

[57] ABSTRACT

A bandage includes a longitudinal elastic strip, which has a center region, and wherein a first flap extends substantially at right angles outwardly in one direction from the longitudinal strip near one end thereof. The first flap has an inner side, and is formed with a substantially V-shaped notch. A padding is provided on the inner side of the first flap, and a second flap extends outwardly near the one end of the strip in a direction opposite to the one direction. A first Velcro TM patch is provided on the outer side of the first flap, and a second Velcro TM patch is provided on the inner side of the second flap, the strip having an end region opposite to the one end. The V-shaped notch faces the end region. A third Velcro TM patch is provided at the center region of the strip on an outer side thereof, and a fourth Velcro TM patch is provided at the end region of the strip on an inner side thereof. Hence the first flap may be attached to the second flap, while looping around the hallux, so that an apex of the V-shaped notch faces the second toe, permitting the strip to be wrapped around the posterior aspect of the calcaneous, thereafter to pass dorsally near the mid tarsal joint, and be wrapped around the lateral aspect, so that the end region of the strip may be attached to the strip's center region, thereby forcing the big toe outwardly, and relieving bunion pain.

7 Claims, 5 Drawing Figures

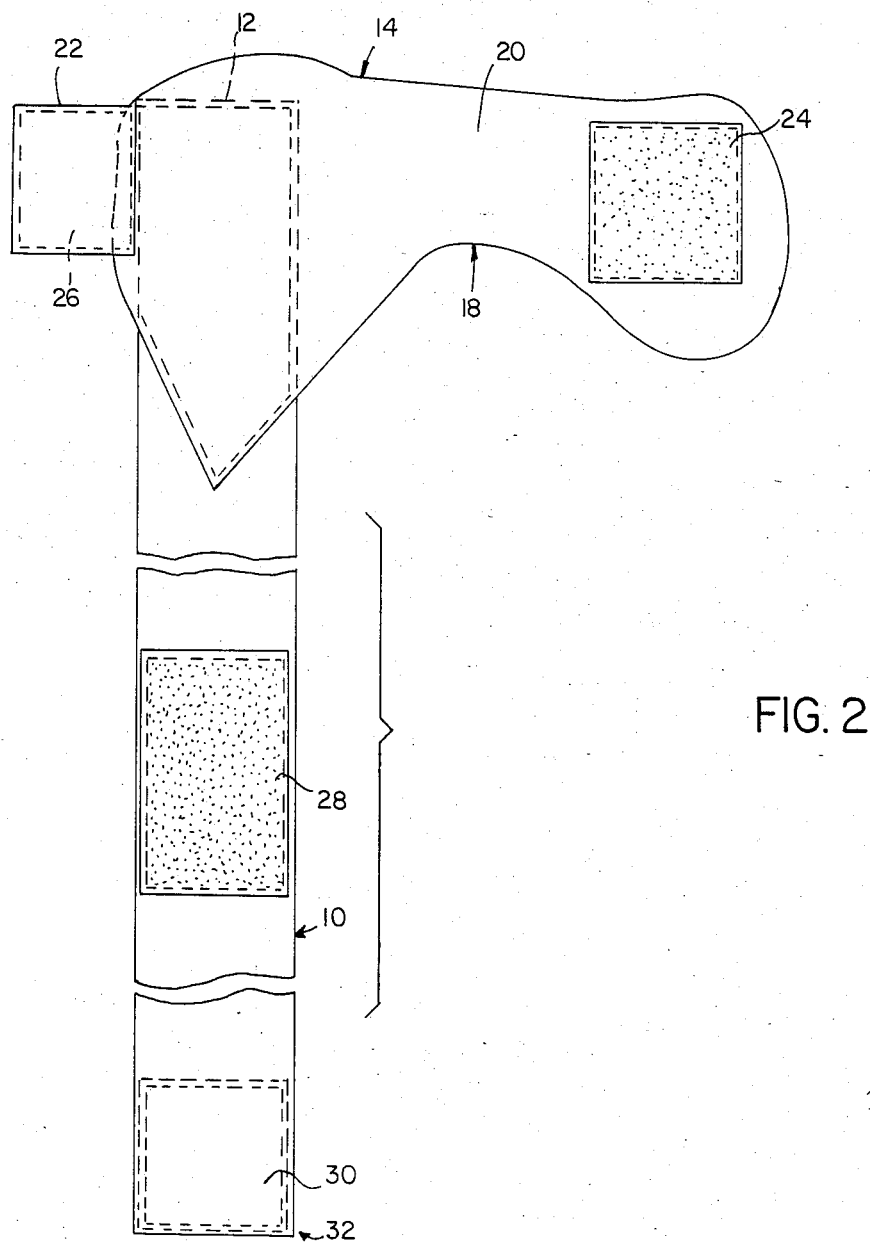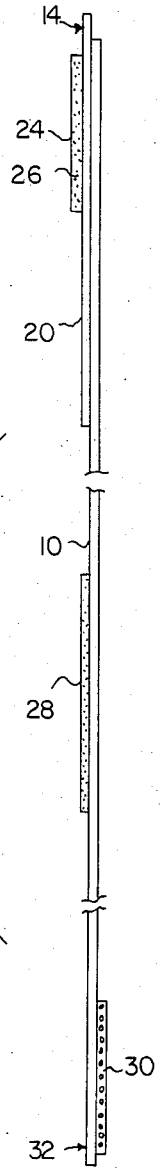

BANDAGE TO REDUCE BUNION PAIN THEREWITH

BACKGROUND OF THE INVENTION

In a normal foot the musculature and bone alignment are evenly distributed, but painful bunions develop from bone and muscle imbalances that cause the big toe to move inwardly, and force the joint out of alignment.

In severe cases surgery to relieve this problem is indicated, but many, and particularly early cases of this disease can be treated by less drastic methods.

Thus attempts to relieve bunion pain have been made by using so-called bunion splints. Bunion splints of this type are shown, for example, on page 53 of the catalog of the Mayflower Podiatry Supply Co., Inc. One type of that splint permits valgus control with great toe flexion, and is primarily used when non-ambulatory exercise is indicated. Another type of that splint provides positive control for immediate post-operative immobilization. It permits adjustable lever action for lateral and dorsal plantar positioning. Relief of bunion pain has also been sought by means of a cross-over arch/ankle brace illustrated, for example, on page 52 of the aforesaid catalog. The relief of bunion pain is, however, only a secondary function of the cross-over arch/ankle brace.

The primary function of that one-piece elastic bandage is to provide control for the upper ankle joint, and to provide medial foot support for pes cavus or pes valgus, and alternatively, to provide support for ankle injuries.

SUMMARY OF THE INVENTION

It is accordingly a prime object of the present invention to provide non-surgical superior control and relief of bunion pain by re-aligning any deformed bone structure, and to gently force the big toe to move from its misaligned position to a properly aligned position.

This object is achieved, according to the present invention, by providing a bandage including a longitudinal elastic strip having a center region, wherein a first flap extends substantially at right angles outwardly in one direction from the longitudinal strip near one end thereof, and wherein the first flap has an inner side, and is formed with a substantially V-shaped notch, tissue protection means provided on the inner side of the first flap, a second flap extending outwardly near the one end of the strip in a direction opposite to the one direction, first attachment means including a first Velcro TM patch on the outer side of the first flap, and a second Velcro TM patch on the inner side of the second flap, the strip having an end region opposite to the one end, the V-shaped notch facing the end region, the regions being separated from one another by a predetermined spacing.

Second attachment means include a third Velcro TM patch at the center region of the strip on an outer side thereof, and a fourth Velcro TM patch at the end region of the strip on an inner side thereof.

The novel features which are considered as characteristic of the invention are set forth in particular in the appended claims. The invention itself, however, both as to its construction and method of operation, together with additional objects and advantages thereof, will best be understood from the following description of a preferred embodiment, when read in connection with the accompanying drawings.

BRIEF DESCRIPTION OF THE DRAWING

FIG. 1 is a plan view of the bandage, according to the present invention,

FIG. 2 is a side view of the bandage of FIG. 1,

DESCRIPTION OF THE PREFERRED EMBODIMENT

Figure 3:
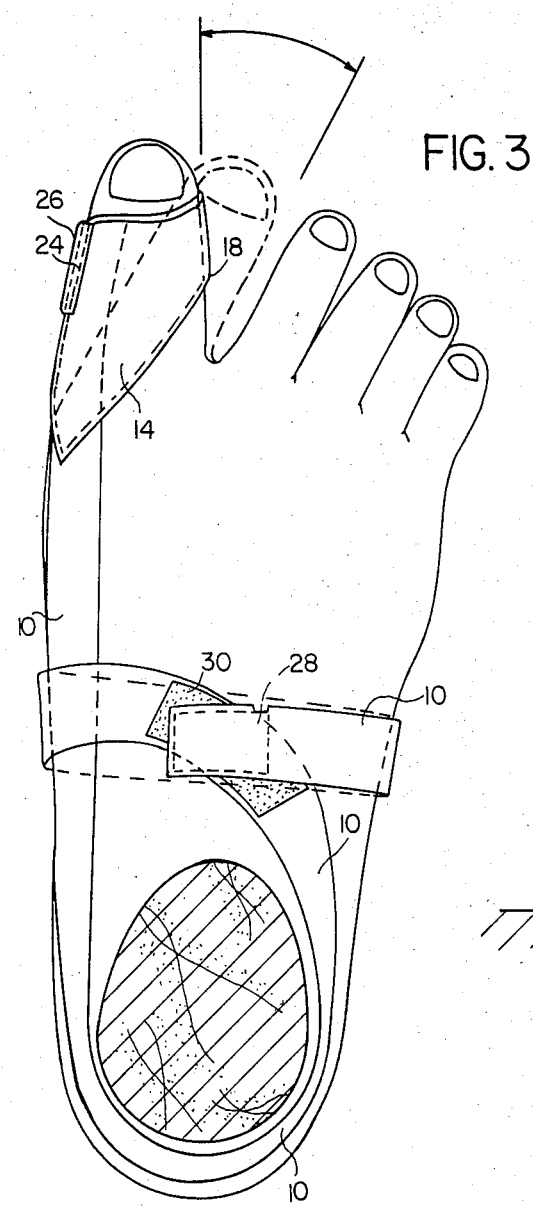
FIG. 3 shows a plan view of a patient's foot, in part section, with the inventive bandage applied thereto.
Figure 4:
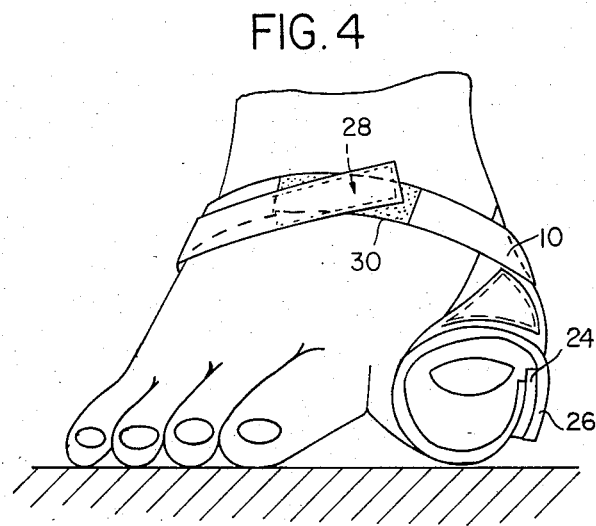
FIG. 4 is a front view of the foot shown in FIG. 3.
Figure 5:
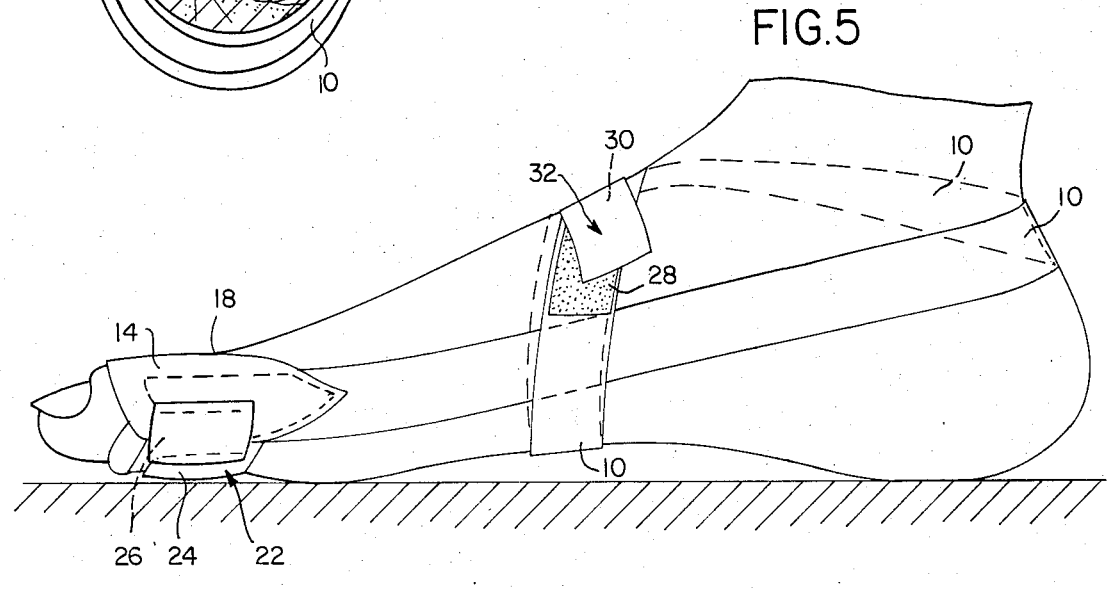
FIG. 5 is a side view of the foot shown in FIGS. 3 and 4.

Referring now to the drawing, a longitudinal elastic strip 10 is provided near an end 12 thereof with a first flap 14, which extends with an outer edge 16 thereof substantially at right angles to the longitudinal direction of the strip 10, and is formed with a substantially V-shaped notch 18. On an inner side of the flap 14 there are provided tissue protection means, for example, in the form of a padding 20. A second, and substantially rectangular flap 22 extends outwardly near the end 12 in a direction opposite to the extension direction of the flap 14 from the strip 10.

In one embodiment attachment means, for example in the form of a Velcro TM patch 24, are provided on an outer side of the flap 14 near an end zone thereof, while a similar Velcro TM patch 26 is provided on an inner side of the second flap 22; it would be equally possible, however, to provide the Velcro TM patch 24 on the inner side of the flap 14, and to provide the Velcro TM patch 26 on the outer side of the flap 22.

The strip 10 defines a center region, which carries on the outer side of the strip another Velcro TM patch 28, while still another Velcro TM patch 30 is attached to the inner side of the strip 10 near an end region 32 thereof, which, in turn, is located opposite to the end 12 of the strip 10.

The length of the strip 10 is tailored to the length of the foot to which it is to be applied, and is generally within a range of about 14 inches to about 22 inches, while its width will advantageously range from about 1 inch to about 2 inches. The spacing of the center region from the end region 32 will in general range from about 7 inches to about 11 inches.

The bandage is applied to the foot of the wearer by looping the first flap 14 around the hallux, or big toe of the patient, with the apex of the V-shaped notch 18 facing the second toe, and thereafter attaching the Velcro TM patch 24 on the flap 14 to the Velcro TM patch 26 on the flap 26. Thereafter the strip 10 is tensioned, and is wrapped under tension about the posterior aspect of the calcaneous, namely the heel, then dorsally near the mid tarsal joint, i.e. under the arch of the foot, and subsequently, as it emerges upwardly from under the foot's arch, about the foot's lateral aspect. At that point the Velcro TM patch 30 located near the end region 33 of the strip 10 is attached to the Velcro TM patch 28 situated at the center region of the strip 10.

As the spacing of the end region 32 from the center region of the strip 10 has been selected so that the elastic strip, when under tension, opposes valgus, or inwardly directed forces acting on the hallux, or big toe, it not only separates the hallux from the second toe, but substantially reduces bunion pain by not only re-aligning the bones, but also by attempting to correct those muscle problems which are also a primary cause of the bunions, namely the imbalance between the abductor and adductor hallocis musculature.

At the same time the tissue protection means, in the form of the padding 20, protects any inflamed area of the first metatarsal joint, even while an outwardly acting force opposes the valgus force acting on the hallux, or the big toe.

While the invention has been illustrated in preferred embodiments, it is not to be limited to the structures shown, since many variations thereof will be evident to one skilled in the art, and are intended to be encompassed in the present invention as set forth in the following claims.

We claim:

1. A bandage, particularly for relief of bunion pain, comprising in combination, a longitudinal elastic strip having a center region, a first flap extending substantially at right angles outwardly in one direction from said longitudinal strip near one end thereof, having an inner side, and being formed with a substantially V-shaped notch, tissue protection means provided on the inner side of said first flap, a second flap extending outwardly near said one end of said strip in a direction opposite to said one direction, first attachment means provided on at least one of said flaps so that said one of said flaps is attachable to the other of said flaps, while forming a loop therewith, said strip having an end region opposite to said one end, said V-shaped notch facing said end region, said regions being separated from one another by a predetermined spacing, and second attachment means provided at least on one of said regions for attaching said end region to said center region, whereby said first flap is attachable to said second flap by said first attachment means, while looping around the hallux so that an apex of said V-shaped notch faces the second toe, permitting the strip to be wrapped dorsally around the posterior aspect of the calcaneous, thereafter to pass dorsally near the mid tarsal joint, and be wrapped around the lateral aspect, so that said end region of said strip may be attached to said strip center region by said second attachment means, the spacing of said regions from one another being chosen so that the elastic strip, when under tension, opposes valgus forces acting on the hallux, and when the bandage is operatively applied to the foot of a patient, and separates the hallux from the second toe, while said tissue protection means protects any inflamed area of the first metatarsal joint even while said valgus forces act on the hallux, and substantially reduces bunion pain.

2. The bandage as claimed in claim 1, wherein said first attachment means includes a first Velcro TM patch on the outer side of said first flap near an end zone thereof, and a second Velcro TM patch on the inner side of said second flap.

3. The bandage as claimed in claim 1, wherein said first flap extends at right angles outwardly in said one direction with an outer edge thereof, and wherein said tissue protection means includes a padding on the inner side of said first flap.

4. The bandage as claimed in claim 1, wherein said second attachment means includes a third Velcro TM patch at said center region of said strip on an outer side thereof, and a fourth Velcro TM patch at said end region of said strip on an inner side thereof.

5. The bandage as claimed in claim 1, wherein said strip has a length in the range from about 14 to about 22 inches, a width from about 1 inch to 2 inches, and wherein said spacing of said regions is in the range from about 7 inches to about 11 inches.

6. The bandage as claimed in claim 1, wherein said strip and said flaps are machine-stitched to one another.

7. The bandage as claimed in claim 1, wherein said strip and said flaps are hand-sewn to one another.

* * * * *